(12) United States Patent
Kumari

(10) Patent No.: US 11,629,113 B2
(45) Date of Patent: Apr. 18, 2023

(54) PYROGALLOL[2]RESORCIN[2]ARENE

(71) Applicant: University of Cincinnati, Cincinnati, OH (US)

(72) Inventor: Harshita Kumari, Loveland, OH (US)

(73) Assignee: University of Cincinnati, Cincinnati, OH (US)

( * ) Notice: Subject to any disclaimer, the term of this patent is extended or adjusted under 35 U.S.C. 154(b) by 0 days.

(21) Appl. No.: 17/515,891

(22) Filed: Nov. 1, 2021

(65) Prior Publication Data

US 2022/0135508 A1  May 5, 2022

Related U.S. Application Data

(60) Provisional application No. 63/107,761, filed on Oct. 30, 2020.

(51) Int. Cl.
*C07C 37/20* (2006.01)
*C07C 37/84* (2006.01)

(52) U.S. Cl.
CPC .............. *C07C 37/20* (2013.01); *C07C 37/84* (2013.01); *C07C 2521/18* (2013.01); *C07C 2603/52* (2017.05)

(58) Field of Classification Search
CPC ...... C07C 37/20; C07C 37/84; C07C 2603/40
See application file for complete search history.

(56) References Cited

U.S. PATENT DOCUMENTS 5,171,330 A * 12/1992 Santoro .................. C07C 39/17
44/442

OTHER PUBLICATIONS

Funck et al. Microwave-assisted synthesis of resorcin[4]arene and pyrogallol[4]arene macrocycles. Tetrahedron Letters, vol. 51, 6399-6402. (Year: 2010).*
Zhang et al. A M18L6 metal-organic nanocapsule with open windows using mixed macrocycles. Chemical Communication, vol. 54, 635-637. (Year: 2018).*
Yasmin et al. Stereospecific synthesis of resorcin[4]arene and pyrogallol[4]arene in dynamic thin films. Chemical Communication, vol. 49, 10932-10934. (Year: 2013).*
Fowler et al. Introducing Defects into Metal-Seamed Nanocapsules Using Mixed Macrocycles. Journal of the American Chemical Society, vol. 135, 12184-12187. (Year: 2013).*

\* cited by examiner

*Primary Examiner* — Sikarl A Witherspoon
(74) *Attorney, Agent, or Firm* — Brent M. Peebles

(57) ABSTRACT

A one pot synthesis of a mixed macrocycle of resorcinol and pyrogallol is disclosed using an acidic catalyst by conventional as well as by microwave assisted methods. Compared with traditional synthesis, the microwave mediated tactic provides a simple, greener route and affords higher compound yields in a shorter period. Moreover, the catalyst can be efficiently reused without any loss in activity.

16 Claims, 6 Drawing Sheets

Mix macrocycle of Pg and RS

PYROGALLOL[2]RESORCIN[2]ARENE

CROSS REFERENCE TO RELATED APPLICATIONS

This application claims priority to U.S. Provisional Application Ser. No. 63/107,761, filed Oct. 30, 2020, which application is hereby incorporated by reference in its entirety.

TECHNICAL FIELD

The present invention relates to the preparation of mixed macrocycles.

BACKGROUND OF THE INVENTION

Jean Marie Lehn and Donald J. Cram received the Nobel prize in supramolecular chemistry in 1987 for the discovery of crown ethers and for coining the term 'supramolecular chemistry'. Macrocyclic chemistry has evolved immensely since then, leading to the discovery of a variety of building blocks, including pillarenes, calixarenes, pyrogallolarenes, resorcinarenes, cucurbiturials, CTVs, dendrimers, etc. A common feature in most building blocks/macrocycles is their unique conformation (cone/partial cone/1,2-alternate/chair/boat) that provides an internal cavity as well as conformational flexibility to adopt to varying shapes and sizes. These attributes have led to the synthesis and subsequent discovery of numerous hydrogen-bonded and metal-seamed nanoassemblies with varying architectures, such as, capsules, tubes, helices, bilayers, etc. The energy penalty utilized in the covalent synthesis or preorganization of a macrocycle provides unique features to macrocycles including the ability to non-covalently interact with metals, ligands and guests and act as biomimics. Although inspired by nature, where non-covalent interactions are the driving force for self-assembly, supramolecular chemistry still lacks the availability of greener methods for synthesis of macrocycles to be used as building blocks. Therefore, a need still exists for alternative greener synthetic methodologies to synthesize a unique class of simple as well as mixed macrocycles.

SUMMARY OF THE INVENTION

In one embodiment, the present invention is composition comprising pyrogallol[2]resorcin[2]arene. In another embodiment, the present invention is a method of making a mixed macrocycle of resorcinol and pyrogallol. The method involves mixing pyrogallol and resorcinol with an aldehyde in a solvent selected from the group consisting of acetonitrile, ethanol, acetone, water and combinations thereof. The mixture is irradiated using microwaves to produce a product and the product is crystallized. The resulting product contains a mixed macrocycle. In one embodiment, the mixture is irradiated in the presence of at least one catalyst selected from the group consisting of concentrated HCl, a macroreticular polystyrene-based sulfonic acid ion exchange resin and sulfonated graphitic carbon nitride. In another embodiment, the catalyst is a macroreticular polystyrene-based sulfonic acid ion exchange resin. In one embodiment, the macroreticular polystyrene-based sulfonic acid ion exchange resin is Ambarlyst-15. In another embodiment, the catalyst is sulfonated graphitic carbon nitride.

In one embodiment, the aldehyde is one carbon higher than the required alkyl length. In another embodiment, the solvent is acetonitrile. In one embodiment, the mixture is irradiated at a temperature of at least 70° C. In another embodiment, the mixture is irradiated at a temperature of at least 80° C. In one embodiment, the mixture is irradiated for at least 10 minutes. In another embodiment, the mixture is irradiated for at least 15 minutes.

In one embodiment, the present invention is a method of making a mixed macrocycle of resorcinol and pyrogallol. The method involves mixing pyrogallol and resorcinol with an aldehyde in a solvent selected from the group consisting of acetonitrile, ethanol, acetone, water and combinations thereof. The mixture is heated in the presence of at least one catalyst selected from the group consisting of concentrated HCl, a macroreticular polystyrene-based sulfonic acid ion exchange resin and sulfonated graphitic carbon nitride, to produce a product, and the product is crystallized. The resulting product contains the mixed macrocycle.

In another embodiment, the catalyst is a macroreticular polystyrene-based sulfonic acid ion exchange resin. In one embodiment, the macroreticular polystyrene-based sulfonic acid ion exchange resin is Ambarlyst-15. In another embodiment, the catalyst is sulfonated graphitic carbon nitride. In one embodiment, the aldehyde is one carbon higher than the required alkyl length. In another embodiment, the solvent is acetonitrile.

DETAILED DESCRIPTION OF THE INVENTION

Figure 1:
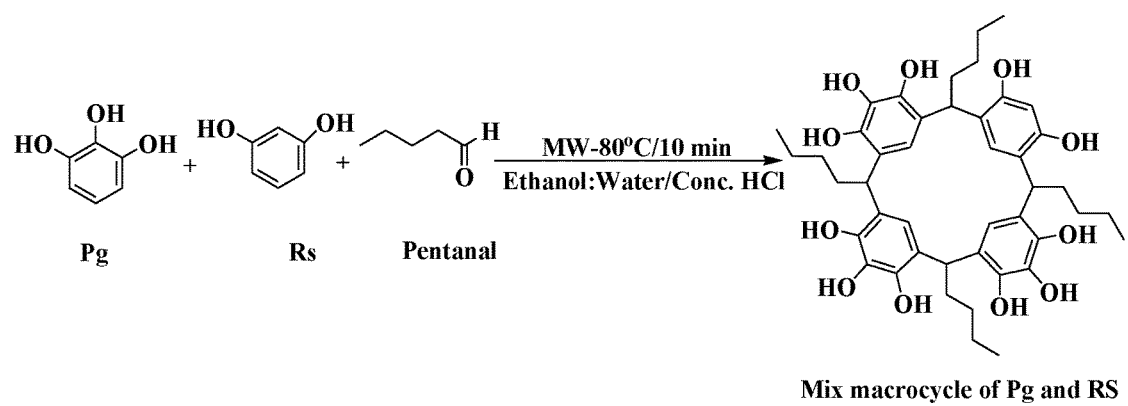
FIG. 1 is a schematic showing the synthesis of a mixed macrocycle of pyrogallol and resorcinol through a microwave mediated tactic.

The details of one or more embodiments of the disclosed subject matter are set forth in this document. Modifications to embodiments described in this document, and other embodiments, will be evident to those of ordinary skill in the art after a study of the information provided herein.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value.

Similarly, when values are expressed as approximations, by use of the antecedent "about," it will be understood that the particular value forms another embodiment.

As used herein, the term "about," when referring to a value or to an amount of mass, weight, time, volume, pH, size, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Resorcinol[4]arene and pyrogallol[4]arene are cyclic oligomers of 1,3-dihydroxybenzene and 1,2,3-trihydroxybenzene derived from an acid reflux condensation reaction of base polyphenolic unit (resorin and pyrogallol) with aldehydes. These can be categorized as subgroups/sister derivatives of calixarenes and have been well established as excellent building blocks to constrict non-covalently driven nanocapsular, nanotubular and MOF-like motifs. Previous studies have reported self-assembly of several metal-seamed nanocapsules of pyrogallolarenes, including mixed-metal (Ga—Co, Ga—Ni, Ga—Co, Ga—Zn) and mixed valent (FeII-FeIII, MnII-MnIII). Resorcinarene, on the other hand, has only been shown to complex with zirconium and silver wherein complexation leads to interlinking between macrocyles.

Interestingly, the mixed macrocycles (MMC) of resorcinol and pyrogallol were shown to either form a bilayer complex or a seven-metallated zinc dimeric nanocapsule. In both of these cases, crystals of 3:1 macrocylic unit were isolated in varying solvents. Although, while showing remarkable self-assembly, the separation of all conformers of mixed macrocycles of Pg and Rs has been very difficult. In addition, the reported methods for the synthesis of pyrogallorene, resorcinarens as well as their mixed macrocycle involve acid catalysis in organic solvents and takes ~12 hours.

In the recent era, as an integral part of green chemistry, microwave mediated organic synthesis (MAOS) has been paid commencing attention in supramolecular chemistry. Mainly, the MAOS techniques are environmentally friendly and offer high yield returns together with ease in processing and handling. Previously, a number of calix[4]arenes macrocycles were reported through microwave assisted methods. However, there have been no reports involving mixed macrocycle synthesis through microwave irradiation.

Earlier, solvent-free methods and acidic catalysts like KOH, 12-tungstophsphoric acid, and P-toluenesulfonic acid have been utilized for the synthesis of various calix[n]arenes. Mainly, catalytic systems are of two major types: homogeneous and heterogeneous. Interestingly, the homogeneous catalysts show high selectivities and high catalytic activity. However, it is difficult to isolate them from the reaction media. The heterogeneous catalytic system has the potential to produce pure product with higher yield in an economical and environmentally-safe manner. Currently, the heterogeneous catalytic system (HCS) has attracted considerable attention. Numerous sustainable HCS were synthesized and utilized successfully for many chemical reactions. Additionally, calix[n]arenes and its derivatives have also been used as potential heterogeneous catalysts for several organic transformation reactions. A variety of catalysts may be used with the present invention to synthesize mixed macrocycles, including concentrated HCl, a macroreticular polystyrene-based sulfonic acid ion exchange resin, such as Ambarlyst-15, and Sg—CN. Using Ambarlyst-15 and Sg—CN catalysts for the MMC is useful, since both work as acidic organo-catalysts and contain strong acidic sulfonic groups. In addition, since they are heterogeneous in nature, they are easily recovered from the reaction.

In one embodiment, the present invention involves a one-pot synthesis of a mixed macrocycle of pyrogallol and resorcinol synthesized efficiently through microwave irradiation. In another embodiment, the same MMC has been synthesized using a heterogeneous catalyst such as Ambarlyst-15 and sulfonated graphitic carbon nitride (Sg—CN). The synthesis may occur under microwave or through conventional heating. However, the previously defined procedure does not produce the anticipated product in the case of a heterogeneous based catalytic system. In one embodiment of the present invention, equivalent amounts of Pg and Rs are combined with aldehyde using different catalysts, such as the heterogeneous catalysts Sg—CN or Ambarlyst. This has been used with different solvent systems and changes in reaction parameters. In one embodiment, the aldehyde is one carbon higher than the required alkyl length. In another embodiment, the aldehyde is valeraldehyde. In one embodiment, the methods of the present invention produce a pyrogallol[2]resorcin[2]arene, specifically, a C-alkyl Pyrogallol[2]resorcin[2]arene macrocycle structure.

Solvents play a commanding feature for scheming and processing of any organic synthesis reaction. Different solvent systems can give different architectures. The physiochemical properties of solvents and catalysts will affect the reaction rate and the product selectivity of synthetic reactions. Solvent properties like polarity, acid/base properties, and protic/aprotic behavior can provide a variety of benefits. Different solvents may be used in the present invention, including ethanol, acetone, water, and/or acetonitrile. These various solvents were used with Ambarlyst-15 and sulfonated graphitic carbon-nitride (Sg—CN) heterogeneous catalyst in different ratios with moderate temperature range and time. Using acetonitrile, the mixed macrocycle of pyrogallol and resorcinol [4]arene was synthesized efficiently. Similarly, using a heterogeneous catalytic system under microwave the mixed macrocycle was obtained in high to excellent yields with shorter reaction times relative to the conventional heating system. Additionally, the catalyst could be recovered in five catalytic cycles without significant loss of catalytic activity.

The Pg, Rs, aldehyde mixture of the present invention may be irradiated using microwaves or heated conventionally. In one embodiment, the mixture is irradiated at a temperature of at least 70° C. In another embodiment, the mixture is irradiated at a temperature of at least 80° C. In one embodiment, the mixture is irradiated for at least 10 minutes. In another embodiment, the mixture is irradiated for at least 15 minutes.

In one embodiment of the present invention, a useful and greener route for the synthesis of a mixed macrocycle of resorcinol and pyrogallol is disclosed that uses an acidic organo-catalyst like Ambarlyst-15 or Sg—CN. These heterogeneous acidic catalysts are cost-effective, recyclable, and easy to use and give higher yields. Moreover, for the first time, the application of MMC has been demonstrated in the synthesis of cyclic carbonates in quantitative yields.

Uses for the MMC

The present invention addresses a need for a new building block that can lead to formation of a library of hydrogen and metal-bonded nanoassemblies for a variety of applications. The novel molecule of the present invention can be used for applications including imaging, and as a nanovehicle for carrying all sorts of actives (drugs/fluorophores, perfume, flavors, photoactives, gases, etc) that can fit within the cavity. The building block of the present invention can be used to create a library of nanostructures (capsules, tubes, ellipsoids) which can be used for gas separation, sorption (clean energy), actives (basically any pertaining to food, cosmetics, pharmaceutics). Also, it can be metallated and used for imaging/therapeutics etc. For example, the macrocycle can be metallated with one or more of the following metals: Zn, Cu, Cr, V, Ti, Co, Fe, Mn, Ni, Ga, In, GaZn, GaNi, GaCo, GaCd, GaAg, GaRb, GaK, Rb, K, Ag, Ho, Ce, Tl, Zr, Ca, Mg, Cd, Cs, GaCs. In addition, a novel synthesis method was developed for this molecule, since traditional methods don't lead to isolation of this isomer.

Various pharmaceutically-active agents to which the invention may be applied include (1) vaccines to protect against diseases such as tetanus, diphtheria, or whooping cough; (2) growth factors, hormones, and neurotransmitters, e.g. insulin, substance P, adrenaline, LHRH, vasopressin, and oxytocin; and (3) drugs such as anti-cancer agents and antibiotics. Thus, a suitable agent may be administered to humans or other vertebrates to invoke immunity, to supplement hormone levels, to eliminate a disease-causing agent, or to provide a therapeutic effect.

EXAMPLES

The present invention involves the novel approach of producing a mixed macrocycle of pyrogallol and resorcinol [4]arene using acidic heterogeneous catalysis. The approach may involve a microwave process or a conventional method. Equivalent amounts of Pg and Rs are combined with aldehyde to form a slurry of crude compound which was recrystallized by methanol and further characterized by FTIR, XRD, 1H-NMR and X-ray Crystallography.

Figure 2:
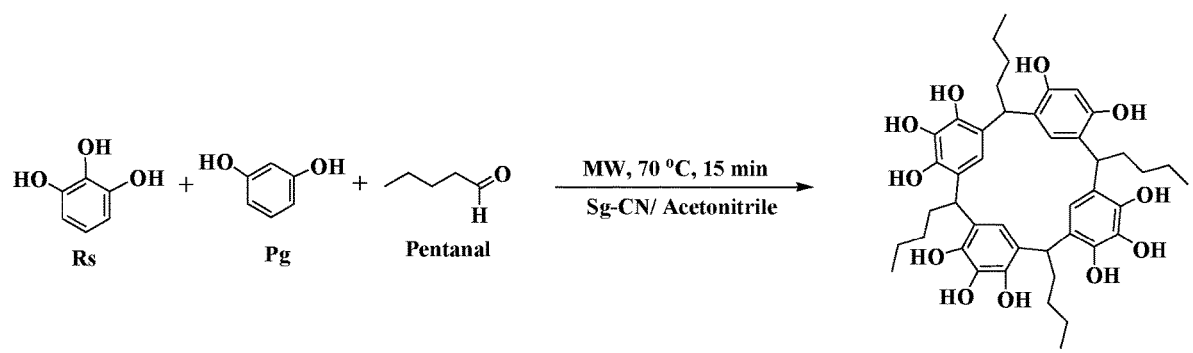
FIG. 2 is a schematic showing the synthesis of a mixed macrocycle of pyrogallol and resorcinol using a solid heterogeneous catalyst.
Figure 3:
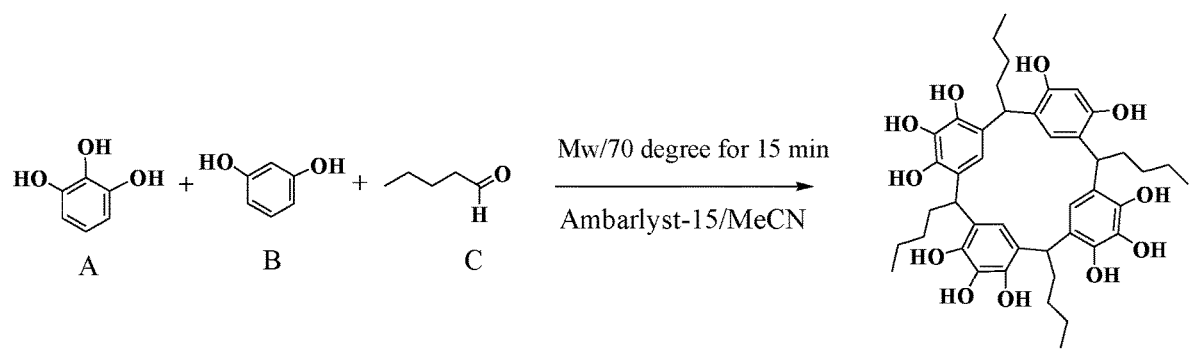
FIG. 3 is a schematic showing the synthesis of a mixed macrocycle of pyrogallol and resorcinol using a solid heterogeneous catalyst.

The overall scheme of synthesizing mixed macrocycle through conventional and microwave mediated methods using homogeneous and solid heterogeneous catalysis is illustrated in FIGS. 1, 2 and 3. Here, the scheme shown in FIG. 1 represents the synthesis of a mixed macrocycle of pyrogallol and resorcinol through a microwave mediated tactic, while the schemes of FIGS. 2 and 3 show alternate embodiments of the procedure using solid heterogeneous catalysts.

Example 1

For the scheme of FIG. 1, an equimolar ratio of pyrogallol and resorcinol with aldehyde was taken in a glass vial with few rubs of conc. HCL and 1:1 ethanol:water mixture then irradiated under microwave for 10 min at 80° C. A slurry of white color crude product formed, which was further recrystallized with methanol.

Example 2

Pyrogallol (5.0 gm) and Resorcinol (4.5 gm) with valeraldehyde (10 ml) was taken with 2 gm of Sg—CN acidic heterogeneous catalyst and 50 ml of acetonitrile solvent. The mixture was refluxed for overnight under study flow of N2 gas. The resultant crystalline ppt was first washed with dichloromethane and then recrystallized with methanol. The catalyst was removed from the reaction mixture washed with methanol dried under vacuum and reused for the next batch.

Example 3

Pyrogallol and Resorcinol with 1 ml of Valeraldehyde and 200 mg of Sg—CN catalyst with 3 ml of MeCN kept under sealed microwave vials and irradiated for 15 min using SP-Synthetic Microwave. The resultant crystalline ppt was first washed with dichloromethane and then recrystallized with methanol.

Example 4

Pyrogallol (5.0 gm) and Resorcinol (4.5 gm) with valeraldehyde (10 ml) was taken with 2 gm of Ambarlyst-15 acidic heterogeneous catalyst and 50 ml of acetonitrile solvent. The mixture was refluxed for overnight under study flow of N2 gas. The resultant crystalline ppt was first washed with dichloromethane and then recrystallized with methanol. The catalyst was removed from the reaction mixture washed with methanol dried under vacuum and reused for the next batch.

Example 5

Pyrogallol and Resorcinol with 1 ml of Valeraldehyde and 200 mg of Ambarlyst-15 catalyst with 3 ml of MeCN kept under sealed microwave vials and irradiate for 15 min using SP-Synthetic Microwave. The resultant crystalline ppt was first washed with dichloromethane and then recrystallized with methanol.

Example 6

For the heterogeneous based catalytic systems (FIGS. 2 and 3), different solvents like ethanol, acetone, water, acetonitrile were used with the heterogeneous catalyst in different ratios with moderate temperature range and time by both conventional as well as the microwave method (see Table 1). Referring to the schemes in FIGS. 2 and 3, an equimolar ratio of pyrogallol and resorcinol with aldehyde was taken in a glass vial with minimum amount of heterogeneous catalyst using acetonitrile as a solvent then irradiated under microwave for 15 min at 70° C. The resultant precipitate was first washed with dichloromethane and then recrystallized with methanol. The catalyst was removed from the reaction mixture and reused for the next batch. The crude compound from all the three methods was taken for further characterization.

TABLE 1

Reaction options for the synthesis of MMC

| Entry | Method | Catalyst | Solvent | Time/Temperature | Yield[a] |
|---|---|---|---|---|---|
| 1 | Conventional | Conc. HCl | Ethanol:water | 24 hours/reflux | 90% |
| 2 | Microwave | Conc. HCl | Ethanol:water | 10 min/80° C. | 96% |
| 3 | Conventional | Sg-CN | Acetonitrile | 24 hours/reflux | 85-90% |
| 4 | Microwave | Sg-CN | Acetonitrile | 15 min/70° C. | 94% |

TABLE 1-continued

Reaction options for the synthesis of MMC

| Entry | Method | Catalyst | Solvent | Time/Temperature | Yield[a] |
|---|---|---|---|---|---|
| 5 | Conventional | Ambarlyst-15 | Acetonitrile | 24 hours/reflux | 85-90% |
| 6 | Microwave | Ambarlyst-15 | Acetonitrile | 15 min/70° C. | 92% |

Reaction condition: a) isolated yield.

Characterization

Figure 4A:
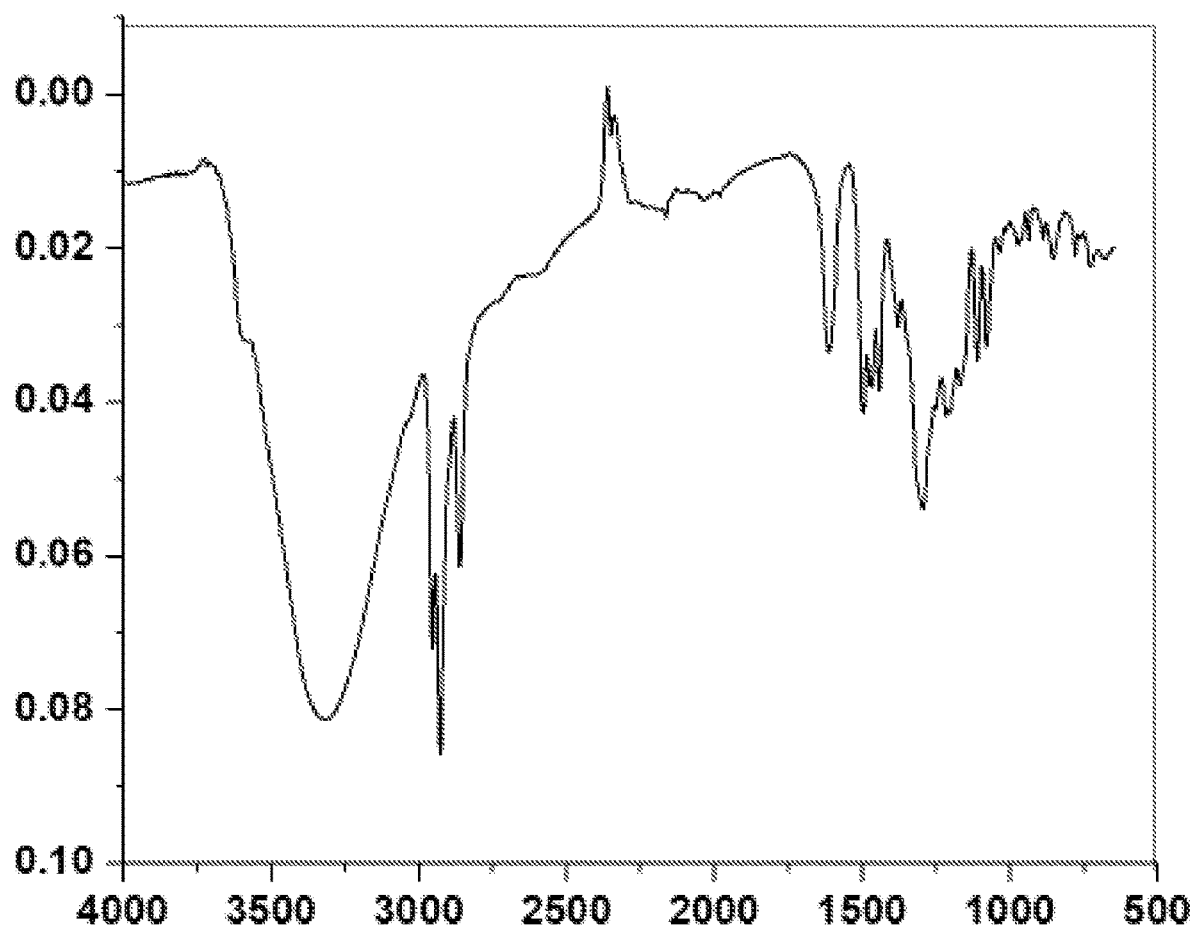
FIG. 4A is an FTIR of an MMC synthesized using microwave irradiation (MW).
Figure 4B:
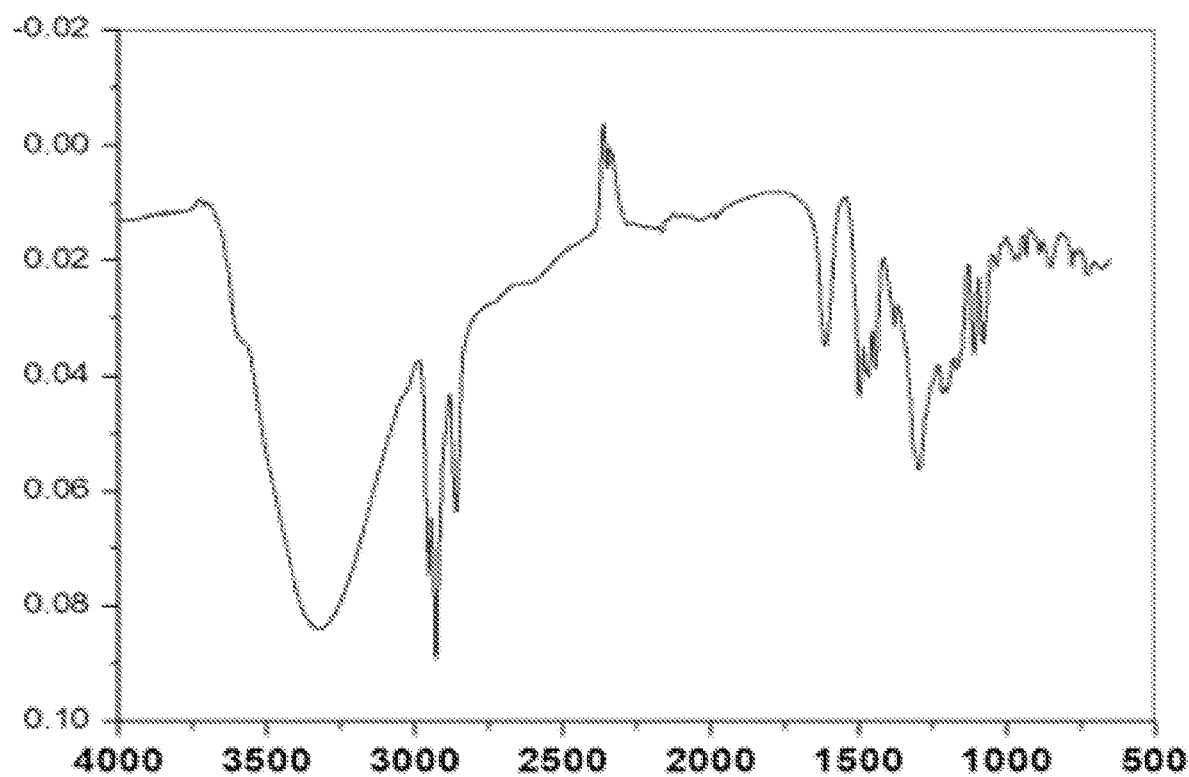
FIG. 4B is an FTIR of acidic heterogenous catalysts catalyzed MMC.

The FTIR of the mixed macrocycle shows the broad overtone peak at 3000-3500 cm-[1] of OH group and C—H stretching peak at 2695-2830 cm-[1] which confirms the presence of functionalization and cyclization of the compound (see FIGS. 4A and 4B). After recrystallization, the compound was further characterized by XRD, $^1$HNMR and X-Ray Crystallography.

Figure 5:
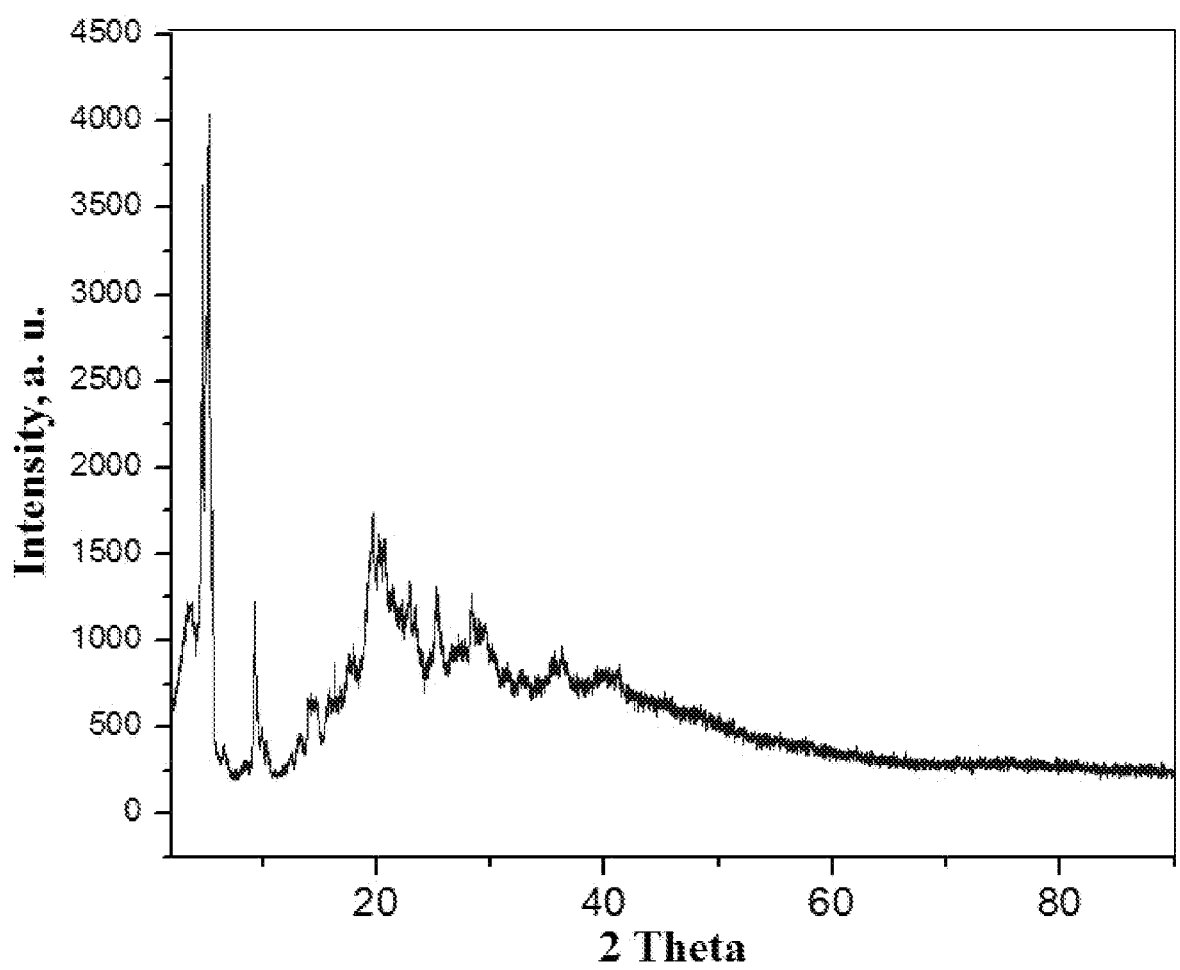
FIG. 5 is an XRD of a MMC synthesized using MW.
Figure 6:
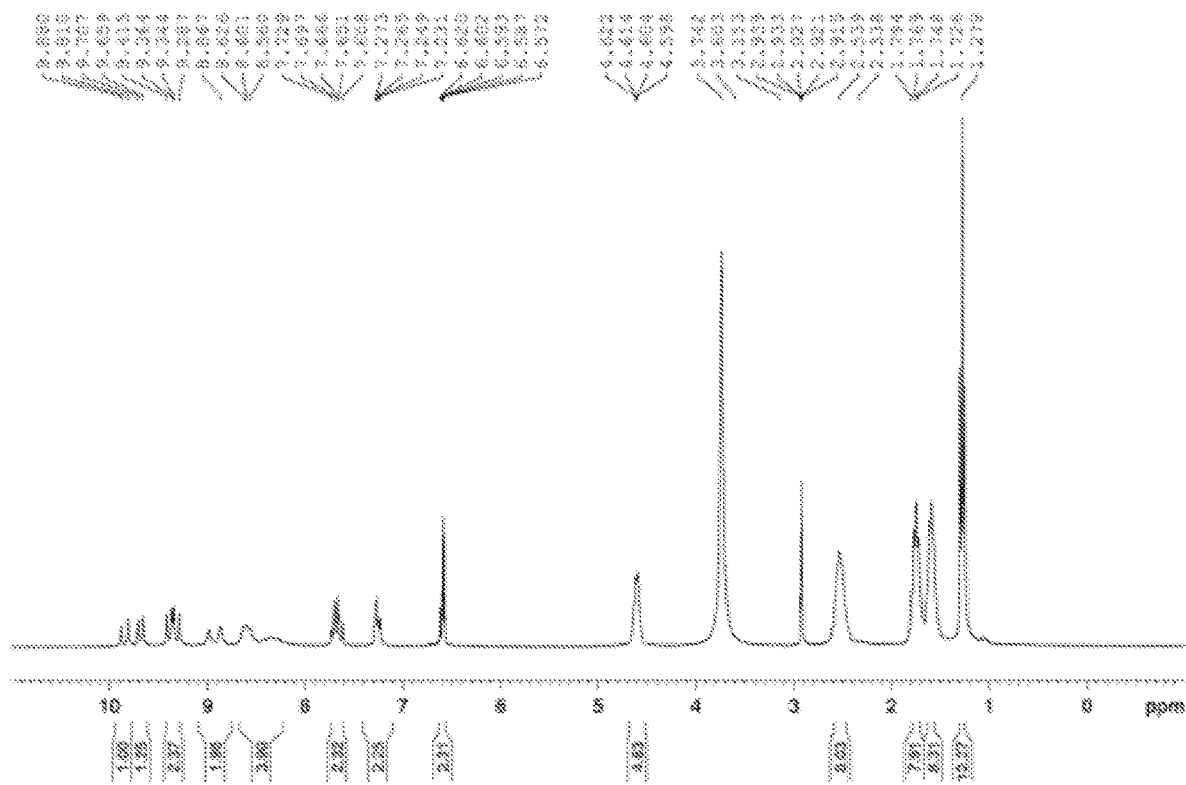
FIG. 6 is $^1$H-NMR Spectra of MMC synthesized through MW.

The XRD-data confirms the crystalline nature of the compound (see FIG. 5) while in the $^1$HNMR spectra, the peak at 4.2 ppm of C—H coupling proton which confirms the cyclization of the reaction. Also, the different peaks of hydroxyl groups were observed between 8-10 PPM which confirms the 1:3 conformer of MMC, (FIG. 6).

Compared to traditional heating systems, the microwave mediated tactic (MW) gives higher yield in minimum amount of time with less impurity. Utilizing this application for chemical transformation to produce mixed macrocycles is a sustainable approach of waste to value added chemicals. Here, the activity of mix macrocycle synthesized thru MW was assessed in the cycloaddition reaction of carbon dioxide with various epoxides for the synthesis of cyclic carbonates. 5.0 mmol of styrene oxide, 200 mg of mix macrocycles as catalyst, tetrabutylammonium iodide (2 mmol) as co-catalyst, were first mixed in 25 ml of acetonitrile. Next, the reaction mixture was transferred into pressure reactor and kept 15 psi $CO_2$ pressure. Afterward, the reaction system was heated at 75° C. for 8 hours for the cycloaddition reaction of CO2 and epoxide. After completion of reaction, reactor was cooled down to room temperature and catalyst was isolated using centrifugation. Mother liquor containing cyclic carbonate as product, evaporated in Rota vapor and purified using column chromatography. Furthermore, corresponding cyclic carbonates were synthesized using a wide range of aromatic and aliphatic epoxides using mix macrocycles and all reactions ensued efficiently in quantitative yields (Table 2).

TABLE 2

| Entry | Epoxides | Products | Yield[b] |
|---|---|---|---|
| 1 | (styrene oxide) | (4-phenyl-1,3-dioxolan-2-one) | 82% |
| 2 | (4-bromostyrene oxide) | (4-(4-bromophenyl)-1,3-dioxolan-2-one) | 80% |
| 3 | (4-chlorostyrene oxide) | (4-(4-chlorophenyl)-1,3-dioxolan-2-one) | 80% |
| 4 | (cyclohexene oxide) | (hexahydrobenzo[d][1,3]dioxol-2-one) | 76% |

The reaction conditions for Table 2: a) Epoxide (5 mol), Tetrabutlyammonium iodide (2 mmol), CO2 (15 psi), MMC (200 mg), acetonitrile, 75° C., 8 h.; b) Isolated yield.

Example 7

An equimolar ratio of pyrogallol and resorcin are mixed with aldehyde (one carbon higher than required alkyl length) in ethanol:water solution. Few drops of conc. HCl is added and the resultant mixture is subjected to microwave synthesis at 80° C. for 10 minutes to obtain a precipitate (product). The product is then crystallized in a methanol:water mixture as well as other solvents. The crystal structure reveals the presence of mixed macrocycle.

Example 8

An equimolar ratio of pyrogallol and resorcin are mixed with aldehyde (one carbon higher than required alkyl length) in acetonitrile. The resultant mixture is subjected to microwave synthesis at 70° C. for 15 minutes in the presence of Sg—CN catalyst to obtain a precipitate (product). Crystallization of product is in process.

Example 9

An equimolar ratio of pyrogallol and resorcin are mixed with aldehyde (one carbon higher than required alkyl length) in acetonitrile. The resultant mixture is subjected to microwave synthesis at 70° C. for 15 minutes in the presence of Ambarlyst-15 catalyst to obtain a precipitate (product). The unit cell of crystals obtained for this product are same as that obtained from method A.

Recycling and Reusability of the Catalyst

The stability and recyclability aspect of catalysts of the present invention were studied. After completion of the reaction both the catalysts were separated, washed with methanol and dried under vacuum and reused for the next set of reactants according to one of the the following processes:

Example 10

Pyrogallol (5.0 gm) and Resorcinol (4.5 gm) with valeraldehyde (10 ml) was taken with 2 gm of Sg—CN acidic heterogeneous catalyst and 50 ml of acetonitrile solvent. The mixture was refluxed for overnight under study flow of N2 gas. The resultant crystalline ppt was first washed with dichloromethane and then recrystallized with methanol. The catalyst was removed from the reaction mixture washed with methanol dried under vacuum and reused for the next batch.

Example 11

Pyrogallol and Resorcinol with 1 ml of Valeraldehyde and 200 mg of Sg—CN catalyst with 3 ml of MeCN kept under sealed microwave vials and irradiated for 15 min using a SP-Synthetic Microwave. The resultant crystalline ppt was first washed with dichloromethane and then recrystallized with methanol.

Example 12

Pyrogallol (5.0 gm) and Resorcinol (4.5 gm) with valeraldehyde (10 ml) was taken with 2 gm of Ambarlyst-15 acidic heterogeneous catalyst and 50 ml of acetonitrile solvent. The mixture was refluxed for overnight under study flow of N2 gas. The resultant crystalline ppt was first washed with dichloromethane and then recrystallized with methanol. The catalyst was removed from the reaction mixture washed with methanol dried under vacuum and reused for the next batch.

Example 13

Pyrogallol and Resorcinol with 1 ml of Valeraldehyde and 200 mg of Ambarlyst-15 catalyst with 3 ml of MeCN was kept under sealed microwave vials and irradiated for 15 min using a SP-Synthetic Microwave. The resultant crystalline ppt was first washed with dichloromethane and then recrystallized with methanol.

The outcome of the recycling experiment confirms that the catalyst can be reused at least 5 times efficiently without any loss in its activity.

Materials and Characterization

All chemicals and solvents were purchased and used without further purification. While, the Sg—CN acidic heterogeneous catalyst was synthesized using reported literature. A theta-theta diffractometer (PANalytical X'Pert Pro, PANalytical B.V.; The Netherlands) with a copper X-ray tube was used to identify crystalline phases of the synthesized solids. The XRD tube was operated at 45 keV and 40 mA for the analyses. Scans were performed over a 2-theta range between 2° to 90° with a step of 0.02° and a one-second count time at each step. Pattern analysis was performed following ASTM procedures using computer software (Materials Data, Incorporated. Jade+v.5-8. XRD Processing Software; Livermore, Calif.) with reference to the 2002 ICDD PDF-2 data files (International Center for Diffraction Data, Incorporated; Newtown Square, Pa.). FTIR analysis was recorded using Agilent Technologies carry 600 series FTIR spectroscopies and NMR was performed using Brucker 300 Ultrashield™.

All documents cited are incorporated herein by reference; the citation of any document is not to be construed as an admission that it is prior art with respect to the present invention.

It is to be further understood that where descriptions of various embodiments use the term "comprising," and/or "including" those skilled in the art would understand that in some specific instances, an embodiment can be alternatively described using language "consisting essentially of" or "consisting of."

While particular embodiments of the present invention have been illustrated and described, it would be obvious to one skilled in the art that various other changes and modifications can be made without departing from the spirit and scope of the invention. It is therefore intended to cover in the appended claims all such changes and modifications that are within the scope of this invention.

What is claimed is:

1. A composition comprising pyrogallol[2]resorcin[2]arene.

2. A method of making a mixed macrocycle of resorcinol and pyrogallol comprising:
   a. mixing pyrogallol and resorcinol with an aldehyde in a solvent selected from the group consisting of acetonitrile, ethanol, acetone, water and combinations thereof;
   b. irradiating the mixture using microwaves to produce a product; and
   c. crystallizing the product;
   wherein the product comprises the mixed macrocycle.

3. The method of claim 2 wherein the mixture is irradiated in the presence of at least one catalyst selected from the group consisting of concentrated HCl, a macroreticular polystyrene-based sulfonic acid ion exchange resin and sulfonated graphitic carbon nitride.

4. The method of claim 3 wherein the catalyst is a macroreticular polystyrene-based sulfonic acid ion exchange resin.

5. The method of claim 3 wherein the catalyst is sulfonated graphitic carbon nitride.

6. The method of claim 2 wherein the aldehyde is one carbon higher than the required alkyl length.

7. The method of claim 2 wherein the solvent is acetonitrile.

8. The method of claim 2 wherein the mixture is irradiated at a temperature of at least 70° C.

9. The method of claim 2 wherein the mixture is irradiated at a temperature of at least 80° C.

10. The method of claim 8 wherein the mixture is irradiated for at least 10 minutes.

11. The method of claim 8 wherein the mixture is irradiated for at least 15 minutes.

12. A method of making a mixed macrocycle of resorcinol and pyrogallol comprising:
    a. mixing pyrogallol and resorcinol with an aldehyde in a solvent selected from the group consisting of acetonitrile, ethanol, acetone, water and combinations thereof;
    b. heating the mixture in the presence of at least one catalyst selected from the group consisting of concentrated HCl, a macroreticular polystyrene-based sulfonic acid ion exchange resin and sulfonated graphitic carbon nitride, to produce a product; and
    c. crystallizing the product;
    wherein the product comprises the mixed macrocycle.

13. The method of claim 12 wherein the catalyst is a macroreticular polystyrene-based sulfonic acid ion exchange resin.

14. The method of claim 12 wherein the catalyst is sulfonated graphitic carbon nitride.

15. The method of claim 12 wherein the aldehyde is one carbon higher than the required alkyl length.

16. The method of claim 12 wherein the solvent is acetonitrile.

* * * * *